United States Patent [19]

Jung et al.

[11] Patent Number: 4,504,478
[45] Date of Patent: Mar. 12, 1985

[54] CEPHALOSPORIN-1-OXIDE DERIVATIVES

[75] Inventors: Frederic H. Jung, Rilly la Montague, France; Gareth M. Davies, Macclesfield, England

[73] Assignees: Imperial Chemical Industries PLC, Enghine-les-Bains, France; ICI Pharma, London, England

[21] Appl. No.: 415,541

[22] Filed: Sep. 7, 1982

[30] Foreign Application Priority Data

Sep. 18, 1982 [EP] European Pat. Off. ........ 81401458.5

[51] Int. Cl.³ .................. A61K 31/545; C07D 501/18
[52] U.S. Cl. .................................... 514/202; 544/22; 544/25; 544/27; 544/28; 514/203; 514/205; 514/206; 514/207
[58] Field of Search .................... 424/246; 544/28, 22, 544/25, 27

[56] References Cited
U.S. PATENT DOCUMENTS 4,358,447 11/1982 Hannah ................................ 544/21

FOREIGN PATENT DOCUMENTS 31708 7/1981 European Pat. Off. .

OTHER PUBLICATIONS de Koning et al., "Stereospecific Synthesis of Biologically Active Cephalosporin R–Sulphoxides" Chap. 17 in Recent Advances in the Chemistry of B-lactam Antibiotics pub. by Chemical Society, London in 1977 as Spec. Pub. 28.

Primary Examiner—Paul M. Coughlan, Jr.
Attorney, Agent, or Firm—Cushman, Darby & Cushman

[57] ABSTRACT

An antibacterial cephalosporin derivative of the formula I:

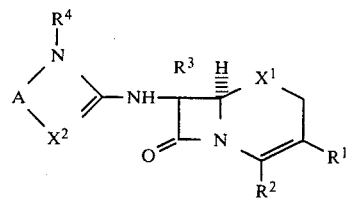

in which
$X^1$ is sulphinyl; $R^1$ is any one of the C-3 substituents from antibacterially-active cephalosporins known in the art; $R^2$ is any one of the C-4 substituents from antibacterially-active cephalosporins known in the art; $R^3$ is hydrogen, 1-6C alkoxy or 1-6C alkylthio; $X^2$ is nitrogen or a radical $N \oplus R^5$; $R^4$ and $R^5$ are a variety of radicals described in the specification; —A— is of the formula II or III:

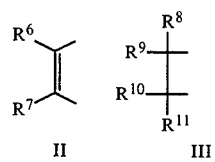

in which $R^6$, $R^7$, $R^8$, $R^9$, $R^{10}$ and $R^{11}$ are a variety of substituents described in the specification; and the pharmaceutically-acceptable acid- and base-addition salts thereof. Pharmaceutical compositions and manufacturing processes are also described.

5 Claims, No Drawings

4,504,478

CEPHALOSPORIN-1-OXIDE DERIVATIVES

This invention relates to cephalosporin derivatives which have antibacterial properties.

The vast majority of therapeutically useful antibiotics based on the penicillin and cephalosporin ring systems have an acylamino radical at the 6β and 7β positions respectively. A number of other substituents at these positions have been investigated but in the main the resulting compounds have at least possessed only weak antibacterial activity. One exception to this generalisation is the amidino substituent. Penicillin derivatives carrying a substituted amidino radical in the 6β position (see for example UK Pat. Nos. 1,315,566 and 1,406,732) have been found to have useful antibacterial acitivity and two such compounds, mecillinam and pivmecillinam, are commercially available. However, the corresponding cephalosporin derivatives have been found to have a surprisingly low level of antibacterial activity. European Patent Publication No. 18595 describes a series of cephalosporin derivatives carrying a 2- or 4-pyridinioamino radical in the 7-position.

Euopean Patent Publications Nos. 31708 and 55562 describe cephalosporin derivatives carrying an imidazolin-2-ylamino or imidazol-2-ylamino radical in the 7-position and a known substituent in the 3-position of the cephalosporin nucleus. The present application represents an extension of this work to cephalosporin derivatives having a sulphinyl radical at the 1-position.

BRIEF DESCRIPTION OF FIGURES OF DRAWING

In the drawing, formulas are given which are identified with Roman Numbers. The formulas are identified with the same Roman Numbers in the following description.

According to the invention there is provided a cephalosporin derivative of the formula I:

[Formula I given hereafter]

in which $X^1$ is sulphinyl;

$R^1$ is any one of the C-3 substituents from anti-bacterially-active cephalosporins known in the art;

$R^2$ is any one of the C-4 substituents from anti-bacterially-active cephalosporins known in the art;

$X^2$ is nitrogen or $N^+R^5$;

$R^3$ is hydrogen, 1-6C alkoxy or 1-6C alkylthio;

$R^4$ and $R^5$, which may be the same or different, are hydrogen, 1-6C alkyl (e.g. methyl), 1-6C alkanoyl (e.g. acetyl), hydroxy, 1-6C alkoxy (e.g. methoxy), amino, 1-6C alkanoylamino (e.g. acetylamino), 1-6C alkylamino (e.g. methylamino), 1-6C aminoalkyl (e.g. 2-aminoethyl), 2-6C hydroxyalkyl (e.g. 2-hydroxyethyl), 2-6C carboxyalkyl (e.g. 2-carboxyethyl), 2-6C alkenyl (e.g. allyl), 3-6C alkoxyalkyl (e.g. methoxymethyl), 3-8C alkoxycarbonylalkyl (e.g. methyoxycarbonylmethyl), furylmethyl, phenyl or 7-11C phenylalkyl (e.g. benzyl), in the latter two of which the phenyl ring is optionally substituted by halogen (e.g. F, Cl, Br), methyl, methoxy, nitro, hydroxy, amino, carboxy or methoxycarbonyl;

—A— is a radical of the formula II or III:

[Formula II]

[Formula III]

in which $R^6$ and $R^7$, which may be the same or different, are 1-6C haloalkyl, 1-6C azidoalkyl, 2-6C cyanoalkyl, 2-6C carboxyalkyl, 3-8C alkoxycarbonylalkyl, 2-6C carbamoylalkyl, 3-8C alkylcarbamoylalkyl, 4-10C dialkylcarbamoylalkyl, 2-6C (amino)(carboxy)alkyl, 2-6C alkenyl, 2-6C nitroalkenyl, 8-15C arylalkenyl, 14-25C diarylalkenyl, 20-35C triarylalkenyl, 1-6C alkylthio, 2-6C aminoalkylthio, 3-8C alkylaminoalkylthio, 4-12C dialkylaminoalkylthio, 2-6C aminoalkoxy, 3-8C alkylaminoalkoxy, 4-12C dialkylaminoalkoxy, 6-10C arylthio, 6-10C aryloxy, 7-11C arylalkyl, amino, 1-6C alkylamino, 2-8C dialkylamino, 6-10C arylamino, 7-11C arylalkylamino, 12-20C diarylamino, 1-6C alkanoyl, 7-11C aroyl, 2-6C alkoxycarbonylamino, 7-11C aryloxycarbonylamino, 2-6C alkoxythiocarbonylamino, 7-11C aryloxythiocarbonylamino, 1-6C alkanoylamino, 7-11C aroylamino, 2-6C alkylureido, 7-11C arylureido, 3-8C hydroxyalkenyl, carbamoyl, 2-6C alkylcarbamoyl, 3-8C dialkylcarbamoyl, 5-10C (dialkylaminoalkyl)carbamoyl, 7-11C arylcarbamoyl, thiocarbamoyl, 2-6C (alkyl)thiocarbamoyl, 3-8C (dialkyl)thiocarbamoyl, 7-11C (aryl)thiocarbamoyl, 5-10C (dialkylaminoalkyl)thiocarbamoyl, 2-6C alkoxyalkyl, 2-6C alkanoyloxyalkyl, 2-6C carbamoyloxyalkyl, 3-8C alkylcarbamoyloxyalkyl, 4-12C dialkylcarbamoyloxyalkyl, 7-11C (aryl)(hydroxy)alkyl, 7-11C (aryl)(amino)alkyl, 2-6C alkanoylaminoalkyl, 3-8C haloalkanoylaminoalkyl, 8-15C aroylaminoalkyl, 2-6C ureidoalkyl, 3-8C (alkylureido)alkyl, 4-12C (dialkylureido)alkyl, 8-15C (arylureido)alkyl, guanidinoalkyl, 2-6C formimidoylaminoalkyl, 3-8C alkylimidoylaminoalkyl, 1-6C alkoxy, formyl, 2-6C formylalkyl, 2-10C alkanesulphonylaminoalkyl, 7-15C arenesulphonylaminoalkyl, 2-6C alkyl substituted on different carbons by two radicals selected from hydroxy, nitro, amino, 1-6C alkylamino, 2-8C dialkylamino, 6-10C arylamino, 7-11C arylalkylamino, 7-15C (aryl)(alkyl)amino, 8-20C (arylalkyl)(alkyl)amino, pyrrolidino, piperidino, piperazino, N-methylpiperazino, morpholino, 1-6C alkoxy, 1-6C alkylthio, 6-10C aryloxy, 6-10C arylthio, 7-11C arylalkoxy and 7-11C arylalkylthio, 2-6C alkyl substituted on one carbon by nitro, amino, 1-6C alkylamino, 2-10C dialkylamino or 1-6C alkanoylamino and on a different carbon by methyl which is itself substituted by two radicals selected from cyano, 2-6C alkoxycarbonyl and 1-6C alkanoyl, radicals of the formula IV, V, VI,, VII, VIII, IX or X:

[Formula IV]

[Formula V]

[Formula VI]

[Formula VII ]

[Formula VIII]

[Formula IX]

[Formula X]

in which Y is oxygen, sulphur or $CH_2$, m is 1 to 6, q is 0 to 6, n is 0 to 2, p is 1 to 4, $R^{12}$ is 1-6C alkyl, 6-10C aryl or 7-11C aralkyl, $R^{13}$ is hydrogen, 1-6C alkyl or 6-10C aryl, $R^{14}$ is hydrogen, 1-6C alkyl, 6-10C aryl, 7-11C arylalkyl or heterocyclyl, $R^{15}$ is hydrogen or 1-6C alkyl which is optionally substituted by carboxy, 2-6C alkoxycarbonyl, carbamoyl or cyano, $R^{16}$ is heterocyclyl, $R^{17}$ is hydroxy or amino, $R^{18}$ is pyridyl, $R^{19}$, $R^{20}$ and $R^{21}$, which may be the same or different, are hydrogen, 1–6C alkyl or 6–10C aryl and $R^{22}$ and $R^{23}$, which may be the same or different, are cyano, nitro, 2–6C alkoxycarbonyl, 7–11C aryloxycarbonyl, 1–6C alkanoyl or 7–11C aroyl, or $R^6$ and $R^7$ are heterocyclic radicals which are linked (to the imidazole ring) by a direct bond or by a methylene or thiomethylene ($SCH_2$) bridge, or $R^6$ and $R^7$ are hydrogen, halogen, 1–6C alkyl, cyano, hydroxy, carboxy, 2–6C alkoxycarbonyl, 1–6C aminoalkyl, 2–10C alkylaminoalkyl, 3–15C dialkylaminoalkyl or 1–6C hydroxyalkyl, or phenyl optionally substituted by 1 or 2 radicals selected from halogen, nitro, amino, hydroxy, carboxy, cyano, 1–6C alkyl and 2–6C alkoxycarbonyl, or $R^6$ and $R^7$ are 1–6C nitroalkyl, 4–8C alkadienyl, 4–8C alkenynyl, 3–10C alkoxycarbonylaminoalkyl, 3–10C alkylcarbamoylalkyl, 4–15C dialkylcarbamoylalkyl, 8–15C arylcarbamoylalkyl, 3–15C heterocyclylcarbonylaminoalkyl, 4–15C heterocyclylalkylcarbonylaminoalkyl, 3–10C alkanoylcarbamoyloxyalkyl, 9–18C aroylcarbamoyloxyalkyl, 4–15C heterocyclylcarbonylcarbamoyloxyalkyl, 8–18C arylcarbamoyloxyalkyl, 3–15C heterocyclylcarbamoyloxyalkyl, 3–10C (haloalkylureido)alkyl, 8–18C (arylureido)alkyl, 3–15C (heterocyclylureiod)alkyl, 3–10C [alkyl(thioureido)]alkyl, 3–10C [haloalkyl(thioureido)]alkyl, 8–18C [aryl(thioureido)]alkyl, 3–15C [heterocyclyl(thioureido)]alkyl, 1-aminocyanomethyl, 1-dimethylaminocyanomethyl, or N-trifluoroacetyl-N-benzylaminomethyl or radicals of the formula XI, XII or XIII:

[Formula XI]

[Formula XII]

[Formula XIII]

in which $R^{14}$ and $R^{15}$ have the meanings given above, B is 2–6C alkenylene, $R^{24}$ is hydrogen, 1–6C alkyl, 6–10C aryl or 4–7C cycloalkyl and $R^{25}$ is carboxy, carbamoyl, 2–6C alkoxycarbonyl or toluene-p-sulphonyl, wherein when $R^6$ or $R^7$ contains an aryl radical, that aryl radical may optionally be substituted by 1 or 2 substituents selected from halogen, nitro, amino, hydroxy, carboxy, cyano, 1–6C alkyl, 2–6C alkoxycarbonyl, sulpho, 1–6C alkoxy, 1–6C haloalkyl, 1–6C alkylsulphamoyl, 2–8C dialkylsulphamoyl and 2–8C dialkylamino, and wherein when $R^6$ or $R^7$ contains a heterocyclic radical that radical is a 5- or 6-membered aromatic or non-aromatic heterocyclic radical which contains 1, 2, 3 or 4 hetero atoms selected from oxygen, nitrogen and sulphur, such ring, where possible, optionally being in the form of the N-oxide and such ring being optionally fused with a benzene ring, and such fused benzene ring and/or (where possible) the heterocyclic ring being optionally substituted by one or two substituents selected from halogen, 1–6C alkyl, hydroxy, 1–6C alkoxy, phenoxy, mercapto, 1–6C alkylthio, phenylthio, carboxy, 2–6C alkoxycarbonyl, phenoxycarbonyl, carbamoyl, 2–6C alkylcarbamoyl, 3–10C dialkylcarbamoyl, phenylcarbamoyl, dipehnylcarbamoyl, nitro, amino, 1–6C alkylamino, 2–8C dialkylamino, phenylamino, 7–12C (phenyl)(alkyl)amino, diphenylamino, carboxyamino, 2–6C (carboxy)(alkyl)amino, (carboxy)(phenyl)amino, 1–6C alkanoylamino, 2–10C (alkanoyl)(alkyl)amino, benzoylamino, 8–14C (benzoyl)(alkyl)amino, cyano, phenyl, sulphamoyl, 1–6C alkylsulphamoyl, 2–10C dialkylsulphamoyl, phenylsulphamoyl, 1–6C haloalkyl, 1–6C aminoalkyl, 2–8C alkylaminoalkyl, 3–12C dialkylaminoalkyl, 2–6C carboxyalkyl, 1–6C sulphoalkyl and oxo; or $R^6$ and $R^7$ are joined to form, together with the carbon atoms to which they are attached, a mono-, bi- or tri-cyclic carbocyclic ring system which may be nonaromatic, partially aromatic or fully aromatic, the aromatic part of such a ring system being optionally substituted by 1, 2 or 3 radicals selected from halogen, hydroxy, amino, cyano, carboxy, carbamoyol, nitro, ureido, 1–6C alkyl, 1–6C alkoxy, 1–6C haloalkyl, 1–6C alkylamino, 1–6C hydroxyalkyl, 1–6C aminoalkyl, 1–6C alkanoylamino, 1–6C azidoalkyl, 2–8C dialkylamino, 2–10C alkylaminoalkyl, 3–15C dialkylaminoalkyl, 2–6C cyanoalkyl, 2–6C carboxyalkyl, 2–6C carbamoylalkyl and 2–6C ureidoalkyl and radicals of the formula XIV, XV, XVI, XVII, XVIII and XIX:

[Formula XIV]

[Formula XV]

[Formula XVI]

[Formula XVII]

[Formula XVIII]

[Formula XIX]

in which $R^{26}$, $R^{27}$, $R^{28}$ and $R^{29}$, which may be the same or different, are hydrogen or 1–6C alkyl; and $R^8$, $R^9$, $R^{10}$ and $R^{11}$, which may be the same or different, are hydrogen, carboxy, cyano, pyridyl, 1–6C alkanoyl, 1–6C hydroxyalkyl, 1–10C alkyl, 7–12C phenoxyalkyl in which the phenyl ring is optionally substituted by diphenylmethyl, or phenyl which is optionally substituted by 1, 2 or 3 radicals selected from halogen, cyano, amino, carboxy, carbamoyl, hydroxy, phenyl, phenoxy, diphenylmethyl, 1–6C alkylamino, 1–6C alkanoylamino, 1–6C alkanesulphonylamino, 1–6C aminoalkyl, 1–6C hydroxyalkyl, 2–10C dialkylamino, 2–6C alkoxycarbonyl, 2–6C alkylcarbamoyl and 3–10C dialkylcarbamoyl; or $R^9$ and $R^{10}$, when in the cis relationship, are joined to form, together with the carbons to which they are attached, a 3 to 6 membered carbocyclic ring, the ring being optionally substituted by 1 or 2 radicals selected from phenyl and 1–6C haloalkyl and the 4 to 6 membered rings optionally containing a double bond in a position other than at the ring fusion; provided that when one of $R^8$, $R^9$, $R^{10}$ and $R^{11}$ is carboxy the remaining members of $R^8$, $R^9$, $R^{10}$ and $R^{11}$ are hdyrogen: and where the compound of the formula I contains a free basic or acidic group, the pharmaceutically-acceptable acid- or base-addition salts respectively thereof.

It is to be understood that in the above formula I and throughout this specification, the illustrated stereochemistry of the ceph-3-em nucleus of the formula XX:

[Formula XX]

is the absolute configuration. It is also to be understood that although the double bond or bonds in the ring attached to the 7-amino group has or have been inserted in particular positions, other tautomeric forms are, in certain instances, possible. Note, however, that the delta-3 double bond is fixed in position. In the sulphinyl radical $X^1$ the oxygen atom may be in the $\alpha$ or $\beta$ configuration, or a mixture of both. When the compound of the formula I contains both an acidic and a basic centre, the compound may exist in the form of a zwitterion.

It will also be observed that, when —A— is a radical of the formula III, the compound of the formula I may contain 1 or 2 carbon atoms, each of which carries non-identical atoms or radicals $R^8$ and $R^9$, and $R^{10}$ and $R^{11}$. When one such carbon atom is present, the compound of the formula I will exist in 2 diastereoisomeric forms. When two such carbon atoms are present, the compound of the formula I will exist in 4 diastereoisomeric forms. It is to be understood that the useful properties, as hereinafter defined, of these diastereoisomers may differ and it is therefore to be understood that when —A— is a radical of the formula III, this invention encompasses the diastereoisomeric mixture represented by the formula I and any individual diastereoisomer which possesses the useful properties, it being a matter of common general knowledge how to obtain such individual diastereoisomers and determine the biological properties of each. Similar remarks apply when the compound of the formula I contains an asymmetric centre in another part of the molecule.

A particular value for $R^1$ is hydrogen, halogen (e.g. fluorine, chlorine or bromine), hydroxy or amino or a saturated or unsaturated, substituted or unsubstituted 1-20C organic group. Illustrative values for $R^1$ when it is a 1-20C organic group are as follows:

(a) 1-6C alkyl, benzyl optionally substituted by fluorine or methoxy, 1-6C haloalkyl, formyl, carboxy, 1-6C alkoxy, 1-6C methylthio, 1-6C alkylamino, phenylamino, benzylamino, 3-6C cycloalkylamino, cyano, 2-6C alkoxycarbonyl, 2-6C alkanoyl, 3-10C alkoxycarbonylalkyl, 2-6C alkoxycarbonylamino, 2-6C alkylthiocarbonylamino, piperidino, pyrolidino, morpholino, 2-6C alkanoylamino, ureido, 2-6C alkylureido, 3-8C dialkylureido, 1-6C alkanesulphinyl, 1-6C alkanesulphonyl, heterocyclyl and heterocyclylthio in which the heterocycle is a 1,3,4-thiadiazol-2-yl or 1,3,4-oxadiazol-2-yl, each optionally substituted in the 5-position, a 1H-tetrazol-5-yl optionally substituted in the 1-position, or a 1H-1,2,3-triazol-4-yl optionally substituted in the 1 or 5 position, the optional substituents in each of these heterocycles being 1-6C alkyl, 1-6C sulphoalkyl, 2-6C carboxyalkyl, 1-6C haloalkyl or 3-6C alkylthioalkyl, or pyridazin-3-yl, oxazol-3-yl or thiazol-3-yl each optionally substituted by 1 or 2 radicals selected from 1-6C alkyl, 1-6C haloalkyl and 2-6C alkoxycarbonyl;

(b) radicals of the formula XXI:

[Formula XXI]

in which $R^{30}$ and $R^{31}$, which may be the same or different, are hydrogen, 1-6C alkyl, 5-7C cycloaliphatic, 6-12C aryl, 7-10C arylalkyl, (e.g. benzyl, 2-phenethyl), formyl, cyano, carboxy, 2-6C alkoxycarbonyl, sulpho, 1-6C alkanesulphinyl, 1-6C alkanesulphonyl, 1-6C alkoxy, 1-6C alkylthio, carbamoyl, nitro, 1-6C hydroxyalkyl, methylcarbamoyloxymethyl, benzylcarbamoyloxymethyl, 2-6C alkoxymethyl, 2-6C alkylthiomethyl, 2-haloethoxymethyl, cyclopentyloxymethyl, benzyloxymethyl or 3-8C alkanoyloxymethyl or radicals of the formula $CH_2SHet^1$ in which $Het^1$ is 1,3,4-thiadiazol-2-yl or 1,3,4-oxadiazol-2-yl both optionally substituted in the 5-position by methyl, 1H-triazol-5-yl optionally substituted in the 1-position by methyl or 1H-1,2,3-triazol-4-yl;

(c) radicals of the formula XXII:

[Formula XXII]

in which $R^{32}$ is cyano, carboxy or 2-6C alkoxycarbonyl;

(d) radicals of the formula XXIII:

[Formula XXIII]

in which $R^{33}$ and $R^{34}$, which may be the same or different, are hydrogen or 1-6C alkyl and e is 1 to 4; and (e) radicals of the formula $CH_2Y$ in which Y is an atom or group which is the residue of a nucleophile or a derivative of a residue of a necleophile, such a nucleophile or a derivative thereof being:

A. 3-15C trialkylamines;

B. heterocyclic means having more than one heteroatom, at least one heteroatom being nitrogen;

C. pyridines which are optionally substituted by 1 to 3 substituents selected from halogen, 1-6C alkyl, 6-10C aryl, 7-11C arylalkyl, 2-10C alkoxyalkyl, 3-10C alkanoyloxymethyl, formyl, carbamoyl, 2-6C alkanoyloxy, 2-6C alkoxycarbonyl, 1-6C alkoxy, 6-10C aryloxy, 7-11C aralkoxy, 1-6C alkylthio, 6-10C arylthio, 7-11C aralkylthio, cyano, hydroxy, 2-6C alkylcarbamoyl, 3-10C dialkylcarbamoyl, 2-6C (hydroxyalkyl) carbamoyl and 2-6C carbamoylalkyl;

D. azide;

E. amino, 1-6C alkanoylamino and 7-11C aroylamino;

F. cyanide, pyrrole and substituted pyrroles;

G. nucleophiles giving rise to $R^1$ of the formula XXIV:

[Formula XXIV]

in which $R^{35}$ and $R^{36}$, which may be the same or different, are selected from hydrogen, cyano, 1-6C alkyl, 2-6C alkoxycarbonyl, 8-20C mono- or di-arylalkoxycarbonyl, 2-6C alkanoyl, 7-11C aralkyl, cyclopentyl and cyclohexyl, and phenyl optionally substituted by 1 or 2 radicals selected from halogen, 1-6C alkyl, 1-6C alkoxy, 1-6C alkylamino, nitro and amino, and $R^{37}$ is selected from hydrogen, 1-6C alkyl, 7-11C aralkyl cyclopentyl and cyclohexyl, and phenyl optionally substituted by 1 to 2 radicals selected from halogen, 1-6C alkyl, 1-6C alkoxy and 1-6C alkylamino;

H. thiourea optionally substituted by 1-6C alkyl, 6-10C aryl, 5-7C alicyclic or heterocyclyl, dithiocarbamates, thioamides substituted by a 1-6C alkyl or 6-10C aryl or thiosemicarbazides, thiosulphates, arylthioacids or heterocyclicthioacids of up to 10 carbons and dithioacids of the formula XXV:

[Formula XXV]

in which $R^{38}$ and $R^{39}$, which may be the same or different, are hydrogen, 1-6C alkyl, 2-6C hydroxyalkyl, 3-8C alkylaminoalkyl, 4-10C dialkylaminoalkyl or phenyl, or $R^{38}$ and $R^{39}$ are joined to form a pyrrolidine, piperidine or morpholine ring or a piperazine ring which is optionally substituted on nitrogen by one or two (in quaternised form) radicals selected from 1-6C alkyl and 3-6C alkenyl;

I. compounds of the formula $R^{40}S(O)_dH$ in which d is 0, 1 or 2 and $R^{40}$ is 1-6C alkyl, 5-7C alicyclic, 6-10C aryl optionally substituted by carboxy, or 7-11C arylalkyl or a 5- or 6-membered heterocyclic ring (partially or fully unsaturated) containing 1 to 4 nitrogens which ring may further include (where possible) oxygen and and/or sulphur, in which the nitrogen may be in the oxide form, which heterocyclic ring may be fused with another heterocyclic ring within the same definition or may be fused with a benzene ring, the above aryl, arylalkyl, heterocyclic or fused benzene ring being optionally substituted (where possible) by 1 or 2 substituents selected from halogen, 1-6C alkyl, 1-6C haloalkyl, 6–10C aryl, 2–6C alkenyl, 1–6C alkoxy, oxo, hydroxy, mercapto, amino, carboxy, cyano, isothiocyanato, carbamoyl, sulphamoyl, 2–6C alkoxycarbonyl, 3–6C alkenyloxycarbonyl, 8–12C aralkylcarbonyl, 7–11C aryloxycarbonyl, 2–6C hydroxyalkyl, 3–6C dihydroxyalkyl, sulphoamino and 1–6C alkanesulphonylamino and radicals of the formula B—$R^{41}$ in which B is a 2–8C straight or branched chain which may be interrupted by a sulphur, oxygen, NH or 1–6C N-alkyl and $R^{41}$ is selected from hydroxy, mercapto, cyano, 1–6C alkylamino, 2–6C dialkylamino, 2–6C alkanoylamino, carboxy, sulpho, carbamoyl, sulphamoyl, amidino, guanidino, 2–6C alkoxycarbonyl, 2–6C alkylcarbamoyl, 2–6C dialkylcarbamoyl, 1–6C alkylsulphamoyl, 2–6C dialkylsulphamoyl, sulphoamino, ureido, 1–6C alkoxy, 1–6C alkylthio, 1–6C alkanesulphonyl, 2–6C alkanoyl and 2–6C alkanoyloxy and radicals of the formula —S—$R^{42}$ in which $R^{42}$ is 1–6C alkyl or a group of the formula B-$R^{41}$ in which B and $R^{41}$ have the meanings given above and radicals of the formula $NR^{43}R^{44}$ in which $R^{43}$ and $R^{44}$, which may be the same or different, are selected from 1–6C alkyl, groups of the formula B-$R^{41}$ in which B and $R^{41}$ have the definitions given above, 1–6C alkoxycarbonyl, 2–6C alkanoyl, carbamoyl, 2–6C alkylcarbamoyl and 3–10C dialkylcarbamoyl;

J. radicals of the formula $R^{45}$—OH in which $R^{45}$ is hydrogen, 1–6C alkyl, 3–6C alkenyl, 3–6C alkynyl, 5–7C cycloalkyl, 6–12C cycloalkylalkyl, 6–10C aryl, 7–11C arylalkyl or furfuryl, any of which may be substituted by 1 or 2 radicals selected from halogen, 1–6C alkyl, nitro, hydroxy, carboxy, 2–6C alkanoyloxy, 2–6C alkoxycarbonyl, 2–6C alkanoyl, 1–6C alkanesulphonyl, 1–6C alkoxysulphonyl, amino, 1–6C alkylamino and 2–6C alkanoylamino, or $R^{45}$ is carbamoyl;

K. radicals of the formula $R^{46}$—Q—COOH in which Q is a direct bond, oxygen, sulphur or NH and $R^{46}$ is:

(i) hydrogen or 1–6C alkyl which may be interrupted by oxygen, sulphur or NH or substituted by a cyano, carboxy, methoxycarbonyl, ethoxycarbonyl, hydroxy, carboxycarbonyl, halogen or amino;

(ii) 2–6C alkenyl which may be interrupted by oxygen, sulphur or NH;

(iii) phenyl, hydroxyphenyl, chlorophenyl, fluorophenyl, tolyl, nitophenyl, aminophenyl, methoxyphenyl, methylthiophenyl, thienyl, pyridyl, cyclohexyl, cyclopentyl, sydnonyl, naphthyl or ethoxynaphthyl; or (iv) $R^{47}$—$(CH_2)_g$ where $R^{47}$ has the value for $R^{46}$ listed in (i) above and g is 1 to 4.

A particular value for $R^2$ is carboxyl, tetrazol-5-yl or a radical of the formula XXVI, XXVII, XXVIII, XXIX, XXX, XXXI, XXXII, XXXIII, XXXIV, XXXV or XXXVI:

[Formula XXVI]
[Formula XXVII]
[Formula XXVIII]
[Formula XXIX]
[Formula XXX]
[Formula XXXI]
[Formula XXXII]
[Formula XXXIII]
[Formula XXXIV]
[Formula XXXV]
[Formula XXXVI]

in which $R^{40}$ is hydrogen or 1–6C alkyl, $R^{41}$ is 1–6C alkyl, $R^{42}$ is hydrogen, 1–6C alkyl, 7–11C arylalkyl or 2–6C alkoxycarbonyl, t is 0 or 1, $R^{43}$ is 1–6C alkyl, 6–10C aryl or 7–11C aralkyl, $R^{44}$ is hydrogen or one, two or three radicals selected from halogen, nitro, cyano, 1–6C alkyl, 1–6C alkoxy, 1–6C alkylthio, 1–6C alkylsulphinyl, 1–6C alkanesulphonyl, 2–6C alkoxycarbonyl, 2–6C alkoxythiocarbonyl, 2–6C alkanoylamino, 6–10C aryl, 6–10C aryloxy, 6–10C arylthio, arylsulphinyl, 6–10C arylsulphonyl, 7–11C aryloxycarbonyl, 7–11C arylthiocarbonyl and 7–11C aryloxythiocarbonyl, $R^{45}$ is hydrogen or one of the values for $R^{43}$ given above and $R^{46}$ is hydrogen or one, two or three radicals selected from halogen, 1–6C alkyl and 1–6C alkoxy.

A particular value for $R^3$ is hydrogen, methoxy or methylthio.

Particular values for $R^6$ and $R^7$, which may be the same or different, are fluoromethyl, chloromethyl, bromomethyl, difluoromethyl, trifluoromethyl, azidomethyl, 3-azidopropyl, cyanomethyl, 2-cyanoethyl, carboxymethyl, 2-carboxyethyl, methoxycarbonylmethyl, carbamoylmethyl, 2-carbamoylethyl, methylcarbamoylmethyl, dimethylcarbamoylmethyl, 2-amino-2-carboxyethyl, vinyl, allyl, 2-nitrovinyl, 2-phenylvinyl, 1-phenylvinyl, 2-phenylallyl, 3-phenylallyl, 2-diphenylvinyl, 2,2diphenylvinyl, 2,3-diphenylallyl, 3,3-diphenylallyl, 1,2,2-triphenylvinyl, 2,3,3-triphenylallyl, methylthio, 2-aminoethylthio, 2-methylaminoethylthio, 2-dimethylaminoethylthio, 2-aminoethoxy, 2-methylaminoethoxy, 2-dimethylaminoethoxy, phenylthio, phenoxy, benzyl, amino, methylamino, dimethylamino, phenylamino, benzylamino, diphenylamino, formyl, acetyl, benzoyl, methoxycarbonylamino, phenoxycarbonylamino, methoxythiocarbonylamino, phenoxythiocarbonylamino, acetylamino, propionylamino, benzoylamino, 3-methylureido, 3-phenylureido, 2-hydroxyprop-1-enyl, carbamoyl, methylcarbamoyl, dimethylcarbamoyl, 2-dimethylaminoethylcarbamoyl, 3-dimethylaminopropylcarbamoyl, phenylcarbamoyl, thiocarbamoyl, (methyl)thiocarbamoyl, (dimethyl)thiocarbamoyl, (phenyl)thiocarbamoyl, 2-dimethylaminoethyl)thiocarbamoyl, methoxymethyl, 2-methoxypropyl, acetoxymethyl, 3-acetoxypropyl, carbamoyloxymethyl, methylcarbamoyloxymethyl, 3-(methylcarbamoyloxy)propyl, dimethylcarbamoyloxymethyl, (phenyl)(hydroxy)methyl, (phenyl)(amino)methyl, acetylaminomethyl, 2-acetylaminoethyl, 3-acetylaminopropyl, 2-trifluoroacetylaminoethyl, 3-trifluoroacetylaminopropyl, benzoylaminomethyl, ureidomethyl, 3-ureidopropyl, (3-methylureido)methyl, 2-(3-methylureido)ethyl, (3,3-dimethylureido)methyl, 3-phenylureido)methyl, guanidinomethyl, ormimidoylaminomethyl, methylimidoylaminomethyl, methoxy, formylmethyl, methanesulphonylaminomethyl, 2-(methanesulphonylamino)ethyl, 3-(methanesulphonylamio)propyl or benzenesulphonylaminomethyl, or ethyl or propyl which are substituted on different carbons by two radicals selected from hydroxy, nitro, amino, methylamino, dimethylamino, phenylamino, benzylamino, (phenyl) (methyl)amino,(benzyl) (methyl)amino, (benzyl) (methyl)amino, pyrrolidino, piperidino, piperazino, N-methylpiperazino, morpholino, methoxy, methylthio, phenoxy, phenylthio, benzyloxy and benzylthio, or ethyl or propyl which are substituted on one carbon by nitro, amino, methylamino, dimethylamino or acetylamino and on a different carbon by methyl which is itself substituted by two radicals selected from cyano, methoxycarbonyl and acetyl, or $R^6$ and $R^7$ are radicals of the formulae IV V, VI, VII, VIII, IX or X given above in which Y is oxygen, sulphur or $CH_2$, m is 1, 2 or 3, q is 0, 1 or 2, n is 0, 1 or 2, p is 1 to 4, $R^{12}$ is methyl, ethyl, phenyl or benzyl, $R^{13}$ is hydrogen, methyl or phenyl, $R^{14}$ is hydrogen, methyl, phenyl, benzyl or heterocyclyl, $R^{15}$ is hydrogen, or methyl or n-propyl optionally substituted by carboxy, methoxycarbonyl, carbamoyl or cyano, $R^{16}$ is heterocyclyl, $R^{17}$ is hydroxy or amino, $R^{18}$ is pyridyl, $R^{19}$, $R^{20}$ and $R^{21}$, which may be the same or different, are hdyrogen, methyl or phenyl, and $R^{22}$ and $R^{23}$, which may be the same or different, are cyano, nitro, methoxycarbonyl, phenoxycarbonyl, acetyl or benzoyl, or heterocyclic radicals which are linked (to the imidazole ring) by a direct bond or by a methylene or thiomethylene ($SCH_2$) bridge, or hydrogen, fluorine, chlorine, bromine, methyl, cyano, hydroxy, carboxy, methoxycarbonyl, aminomethyl, 2-aminoethyl, methylaminomethyl, dimethylaminomethyl, hydroxymenthyl or 2-hydroxyethyl, or phenyl optionally substituted by 1 or 2 radicals selected from fluorine, chlorine, bromine, nitro, amino, hydroxy, carboxy, cyano, methyl and methoxycarbonyl, or 2-nitroethyl, buta-1,4-dienyl, but-1-en-4-ynyl, 2-ethoxycarbonylaminoethyl, 3-isobutoxycarbonylaminopropyl, 2-methylcarbamoylethyl, 2-dimethylcarbamoylethyl, 3-heterocyclylcarbonylaminopropyl, 3-acetylcarbamoyloxypropyl, 3-benzoylcarbamoyloxypropyl, 3-heterocyclylcarbonylcarbamoyloxypropyl, 3-phenylcarbamoyloxypropyl, 3-heterocyclylcarbamoyloxypropyl, 3-[3-(2,2,2-trifluoroethyl)ureido]propyl, 3-(3-phenylureido)propyl, 2-(3-heterocyclylureido)ethyl, 2-[3-(methyl)thioureido]ethyl, 3-[3-(2,2,2-trifluoroethyl)thioureido]propyl, 2-[3-(phenyl)thioureido]ethyl, 2-[3-(heterocyclyl)-thioureido]ethyl, 1-aminocyanomethyl, 1-dimethylaminocyanomethyl or N-trifluoroacetyl-N-benzylaminomethyl, or radicals of the formula XI, XII or XIII given above in which $R^{14}$ and $R^{15}$ have the meanings given above, B is vinylene, $R^{24}$ is hydrogen, methyl, phenyl or cyclohexyl and $R^{25}$ is carboxy, carbamoyl, methoxycarbonyl or toluene-p-sulphonyl, wherein when $R^6$ or $R^7$ contains a phenyl radical, that phenyl may optionally be substituted by 1 or 2 substituents selected from fluorine, chlorine, bromine, nitro, amino, hydroxy, carboxy, cyano, methyl, methoxycarbonyl, sulpho, methoxy, trifluoromethyl, methylsulphamoyl, dimethylsulphamoyl and dimethylamino, and wherein, when $R^6$ or $R^7$ contains a heterocyclic radical, that radical is furan, thiophene, pyrrole, oxazole, thiazole, imidazole, isoxazole, isothiazole, thiadiazole, oxadiazole, triazole, tetrazole, pyridine, pyrimidine, pyrazine, pyridazine or piperazine, such ring, where possible, optionally being in the form of the N-oxide, such ring being optionally fused with a benzene ring and such fused benzene ring and/or (where possible) heterocyclic ring being optionally substituted by one or two substituents selected from fluorine, chlorine, bromine, methyl, ethyl, hydroxy, methoxy, phenoxy, mercapto, methylthio, phenylthio, carboxy, methoxycarbonyl, phenoxycarbonyl, carbamoyl, methylcarbamoyl, dimethylcarbamoyl, phenylcarbamoyl, diphenylcarbamoyl, nitro, amino, methylamino, dimethylamino, phenylamino, (phenyl)(methyl)amino, diphenylamino, carboxyamino, (carboxy)(methyl)amino, (carboxy)(phenyl)amino, acetylamino, (acetyl)(methyl)amino, benzoylamino, (benzoyl)(methyl)amino, cyano, phenyl, sulphamoyl, methylsulphamoyl, dimethylsulphamoyl, phenylsulphamoyl, trifluoromethyl, 2,2,2-trifluoroethyl, 2-aminoethyl, 2-methylaminoethyl, 2-dimethylaminoethyl, 2-carboxyethyl, 2-sulphoethyl and oxo.

A particular value for the ring system formed when $R^6$ and $R^7$ are joined is a cyclobutene, cyclopentene, cyclohexene, cyclohexa-1,3-diene, cyclohexa-1,4-diene or benzene ring or a napththalene or dihydroacenaphthalene ring system.

A particular value for the optional substituent on the aromatic part of the ring system formed by $R^6$ and $R^7$ being joined is 1, 2 or 3 radicals selected from fluorine, chlorine, bromine, hydroxy, amino, cyano, carboxy, carbamoyl, nitro, ureido, methyl, ethyl, n-propyl, isopropyl, methoxy, ethoxy, isopropoxy, fluoromethyl, chloromethyl, trifluoromethyl, trichloromethyl, methylamino, ethylamino, hydroxymethyl, 1-hydroxyethyl, 2-hydroxyethyl, 3-hydroxypropyl, aminomethyl, 1-aminoethyl, 2-aminoethyl, 3-aminopropyl, acetylamino, propionylamino, azidomethyl, 2-azidoethyl, dimethylamino, diethylamino, acetylaminomethyl, methylaminomethyl, ethylaminomethyl, 1-methylaminoethyl, 2-methylaminoethyl, 1-ethylaminoethyl, 2-ethylaminoethyl, dimethylaminoethyl, diethylaminomethyl, 1-dimethylaminoethyl, 2-dimethylaminoethyl, 1-diethylaminoethyl, 2-diethylaminoethyl, cyanomethyl, 1-cyanoethyl, 2-cyanoethyl, carboxymethyl, 1-carboxyethyl, 2-carboxyethyl, carbamoylmethyl, 1-carbamoylethyl, 2-carbamoylethyl, ureidomethyl, 1-ureidoethyl, 2-ureidoethyl, a radical of the formula XIV, a radical of the formula XV, a radical of the formula XVI in which $R^{26}$, $R^{27}$, $R^{28}$ and $R^{29}$ are all hydrogen of one or more of $R^{26}$, $R^{27}$, $R^{28}$ and $R^{29}$ are methyl, a radica of the formula XVII, a radical of the formula XVIII and a radical of the formula XIX.

A particular value for $R^8$, $R^9$, $R^{10}$ or $R^{11}$ is hydrogen, cyano, carbamoyl, methoxycarbonyl, aminomethyl, 2-pyridyl, 3-pyridyl, 4-pyridyl, acetyl, propionyl, hydroxymethyl, 1-hydroxyethyl, 2-hydroxyethyl, 3-hydroxypropyl, methyl, ethyl, n-propyl, i-propyl, n-butyl, n-hexyl, phenoxymethyl, 1-phenoxyethyl, 2-phenoxyethyl, (diphenylmethyl)phenoxymethyl, phenyl, 2-, 3- or 4-fluorophenyl, 2-, 3- or 4-chlorophenyl, 2-, 3- or 4-bromophenyl, 2-, 3- or 4-cyanophenyl, 2-, 3- or 4-aminophenyl, 2-, 3- or 4-carboxyphenyl, 2-, 3- or 4-carbamoylphenyl, 2-, 3- or 4-hydroxyphenyl, 3,4-dihydroxyphenyl, 2-, 3- or 4-phenylphenyl, 2-, 3- or 4-phenoxyphenyl, 2-, 3- or 4-diphenylmethylphenyl, 2-, 3- or 4-methylaminophenyl, 2-, 3- or 4-acetylaminophenyl, 2-, 3- or 4-methanesulphonylaminophenyl, 2-, 3- or 4-aminomethylphenyl, 2-, or 4-(2-aminoethyl)-phenyl, 2-, 3- or 4-hydroxymethylphenyl, 2-, 3- or 4-dimethylaminophenyl, 2-, 3- or 4-diethylaminophenyl, 2-, 3- or 4-methoxycarbonylphenyl, 2-, 3- or 4-ethoxycarbonylphenyl, 2-, 3- or 4-methylcarbamoylphenyl, 2-, 3- or 4-ethylcarbamoylphenyl, 2-, 3- or 4-dimethylcarbamoylphenyl, or 2-, 3- or 4-diethylcarbamoylphenyl, or $R^9$ and $R^{10}$, when in the cis relationship, are joined to form, together with the carbons to which they are attached, a cyclopropane, cyclobutane, cyclobutene, cyclopentane, cyclopentene, cyclohexane, cyclohex-3-ene, cyclohex-4-ene, 3-phenylcyclopropane, 3,3-diphenylcyclopropane, 3-trifluoromethylcyclopropane, 3,3-di(trifluoromethyl)cyclopropane, 3-phenyl-3-trifluoromethylcyclopropane, 3-phenylcyclobutane, 3,3-diphenylcyclobutane, 3,4-diphenylcyclobutane, 3-trifluoromethylcyclobutane, 3,3-di(trifluoromethyl)cyclobutane, 3,4-di(trifluoromethyl)cyclobutane, 3-phenylcyclobut-3-ene, 3,4-diphenylcyclobut-3-ene, 3-trifluorocyclobut-3-ene, 3,4-di(trifluoro)cyclobut-3-ene, 3-phenylcyclohexane, 3,3-diphenylcyclohexane, 3,4-diphenylcyclohexane, 3-trifluorocyclohexane or 3,4-ditrifluorocyclohexane ring, or $R^8$ is carboxy and $R^9$, $R^{10}$ and $R^{11}$ are hydrogen.

The following are nine preferred features of the cephalosporin derivative of the formula I. When any one of these features is taken, either singly or in combination, with the other general features of the cephalosporin derivatives of the formula I listed above, there are obtained preferred sub groups of compounds within the above general definition.

1. $R^1$ is hydrogen, chlorine, methyl, acetoxymethyl, 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-isopropyl-1H-tetrazol-5-ylthiomethyl, 1-(2,2,2-trifluoro)ethyl-1H-tetrazol-5-ylthiomethyl, 1-phenyl-1H-tetrazol-5-ylthiomethyl, 1-(2-methylthio)ethyl-1H-tetrazol-5-ylthiomethyl, 1,3,4-thiadiazol-2-ylthiomethyl, 5-methyl-1,3,4-thiadiazol-2-ylthiomethyl, 1,2,3-thiadiazol-5-ylthiomethyl, 1H-1,2,3-triazol-4-ylthiomethyl, 5-trifluoromethyl-1 H-1,2,4-triazol-3-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-carboxymethyl-7-hydroxypyrrolo-[1,2-b]pyridazin-2-yl)thiomethyl, methoxymethyl, hydroxymethyl, azidomethyl, aminomethyl, benzoyloxymethyl, acetylaminomethyl, carbamoyloxymethyl, 2-methylthio-1,3,4-thiadiazol-5-ylthiomethyl, 2-mercapto-1,3,4-thiadiazol-5-ylthiomethyl, 2-acetylamino-1,3,4-thiadiazol-5-ylthiomethyl, 5-methyl-1,2,4-thiadiazol-2-ylthiomethyl, 2-sulphomethyl-1,2,4-oxadiazol-5-ylthiomethyl, 4-methyl-5-(3-carboxypropyl)thiazol-2-ylthiomethyl, 2H-2-methyl-1,2,3-triazol-4-ylthiomethyl, 1H-1,2,4-triazol-2-ylthiomethyl, 4,5-dihydro-6-hydroxy-4-methyl-5-oxo-1,2,4-triazin-3-ylthiomethyl, 2,5-dihydro-6-hydroxy-2-methyl-5-oxo-1,2,4-triazin-3-ylthiomethyl, 1-oxidopyrid-2-ylthiomethyl, imidazo[4,5-b]pyrid-2-ylthiomethyl or imidazo[4,5-b]pyrimidin-2-ylthiomethyl.

2. $R^1$ is 1H-1,2,3-triazol-4-ylthiomethyl, methyl or acetoxymethyl.

3. $R^1$ is acetoxymethyl.

4. $R^2$ is carboxy.

5. $R^3$ is hydrogen.

6. $X^2$ is nitrogen.

7. $R^4$ is hydrogen.

8. —A— is a radical of the formula II.

9. —A— is a radical of the formula II in which $R^6$ and $R^7$ are hydrogen.

The preferred compound of the invention is 3-acetoxymethyl-7-(imidazol-2-yl)aminoceph-3em-1β-oxide-4-carboxylic acid, and the pharmaceutically acceptable acid-addition salts and base-addition salts thereof.

A suitable acid-addition salt of the cephalosporin derivative of the invention is, for example, a salt formed with hydrochloric, hydrobromic, phosphoric, sulphuric, citric or maleic acid. A suitable base-addition salt of the cephalosporin derivative of the invention is, for example, an alkali metal salt (e.g. a sodium or potassium salt), an alkaline earth metal salt (e.g. a calcium or magnesium salt), or a salt with a primary, secondary or tertiary organic amine (e.g. triethylamine, procaine, dibenzylamine and N,N¹-dibenzyl ethylenediamine, and other amines which have been used to form salts with cephalosporins).

The cephalosporin derivative of the formula I may be manufactured by methods known in themselves for the manufacture of chemically analogous compounds. The following processes, $R^1$, $R^2$, $R^3$, $R^4$, $X^2$, $X^2$ and —A— having the meanings stated above, unless indicated otherwise, are therefore provided as further features of the invention.

The process of the invention is characterised by:

(a) for those compounds in which $R^2$ is a carboxy radical or a heterocyclic radical carrying an acidic proton, and there is optionally a carboxy radical in another part of the molecule, deprotection of the corresponding compound which carries a protecting group, or groups, in place of the acidic hydrogen atom, or atoms. When $R^2$ is a carboxy radical a particularly useful protecting group is the diphenylmethyl or p-methoxybenzyl radical. Such a protecting group may be removed by treatment with a strong organic acid, for example trifluoroacetic acid. A further particularly useful protecting group is the t-butyl radical. This protecting group may be removed by treatment with a strong organic acid such as trifluoroacetic or formic acid. The process may be conducted in the presence of excess organic acid as diluent or solvent or in the presence of an additional diluent or solvent such as anisole or toluene. The process is preferably conducted at or below ambient temperature and preferably over a period of from 5 minutes to 5 hours. Other useful protecting groups are the trimethylsilyl radical (removed by water), the benzyl and substituted benzyl radicals, for example the p-nitrobenzyl or p-methoxybenzyl radical (removed by hydrogenolysis) and the 2,2,2-trichloroethyl radical (removed by zinc/acetic acid).

(b) reaction of a compound of the formula XXXVII:

[Formula XXXVII]

with a compound of the formula XXXVIII:

[Formula XXXVIII]

in which $R^{47}$ is a displaceable radical. $R^{47}$ is for example a halogen atom, preferably a fluorine or chlorine atom. The reaction is preferably conducted in the presence of at least one equivalent of an acid in order that the compound of the formula XXXVIII is in the protonated form. The reaction may be conducted in the presence of a diluent or solvent, for example acetonitrile, dimethylformamide or tetrahydrofuran or mixtures of these and it may be accelerated or completed by the application of heat, for example by heating to 85° or to the boiling point of the diluent or solvent. When $X^2$ is a nitrogen atom and —A— is a radical of the formula II, the compound of the formula XXXVIII may conveniently be prepared in situ by prior reaction of the corresponding N-triphenylmethyl derivative with toluene-p-sulphonic acid. The compound of the formula XXXVII is then added to the reaction mixture.

(c) oxidation of a compound of the formula XXXIX:

[Formula XXXIX]

A suitable oxidising agent is, for example, a peracid, for example peracetic or 3-chloroperbenzoic acid. The reaction may be conducted in a diluent or solvent such as acetic acid.

When the process of the invention manufactures the compound of the formula I in the form of the free acid or free base, or the zwitterion, and a salt is required, the compound of the formula I in the free acid or zwitterionic form is reacted with a base which affords a pharmaceutically-acceptable cation, or the compound of the formula I in the free base or zwitterionic form is reacted with an acid which affords a pharmaceutically-acceptable anion. When the process of the invention manufactures the compound of the formula I in the form of an acid-addition salt and the zwitterionic form is required, the compound of the formula I in the form of an acid-addition salt is reacted with a low molecular weight epoxide such as epoxypropane.

The starting material for use in process (a) may be prepared by a reaction similar to that described in process (b), using a 7-aminocephalosporin derivative which carries a suitable protecting group, for example as described in Example 3.

The starting material of the formula XXXIX for use in process (c) may be prepared by the general methods described in European Patent Publications Nos. 31708 and 55562, and as described in Example 2.

As noted above the cephalosporin derivative of the invention has antibacterial properties, having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system.

The antibacterial properties of the compounds of the invention may also be demonstrated in conventional mouse protection tests.

The results set out in the following Table of the compound described in Example 1 are illustrative of the biological activity of the compounds of the present invention. The results are those obtained on a standard in vitro test system using Jewell and Pearmain agar medium. The antibacterial activity is described in terms of the minimum inhibitory concentration (MIC) determined by agar - dilution technique with an inoculum size of ~$10^5$ CFU.

| Organism | Code No. | MIC µg/ml |
|---|---|---|
| Strep. pyrogenes | A1 | 64 |
| Staph. aureus | A6 | >128 |
| E. coli | A8 | 2 |
| Salmonella dublin | A20 | 1 |
| K. aerogenes | A10 | 4 |
| Ent. cloacae | A13 | 2 |
| Serratia marescens | A16 | 64 |
| Proteus mirabilis | A18 | >128 |
| Ps. aeruginosa | A21 | >128 |

According to a further feature of the invention there is provided a pharmaceutical composition which comprises a cephalosporin derivative of the invention in association with a non-toxic pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one or more known drugs selected from other clinically useful antibacterial agents (for example other β-lactams or aminoglycosides), inhibitors of β-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.5 to 50 g., and preferably 0.5 to 10 g., of the cephalosporin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The cephalosporin derivative of the invention is also a useful intermediate for preparing the cephalosporin derivatives of European Patent Publications Nos. 31708 and 55562. Such a preparation may be accomplished by methods known in the cephalosporin art for reducing a sulphinyl radical at the 1-position to the corresponding sulphur atom.

The invention is illustrated, but not limited, by the following Examples. The n.m.r. spectra are quoted in δ relative to tetramethylsilane (δ=0) as internal standard, (s=singlet, d=doublet, t=triplet, m=multiplet, br=broad). The temperatures are in degrees Centigrade.

EXAMPLE 1

To a solution of 3-acetoxymethyl-7-(imidazol-2-yl)aminoceph-3-em-4-carboxylic acid trifluoroacetate (200 mg.) in acetic acid (10 ml.) cooled to 10° was dropwise added peracetic acid (120 μl.). The temperature was allowed to rise to ambient temperature and the mixture was stirred for 2.5 hours. Insoluble material was removed by filtration and the filtrate was evaporated to dryness in vacuo. Toluene was added to the residue, and then evaporated to dryness in vacuo. The residue was dissolved in the minimum amount of methanol and ether added to give the product as a pale beige powder (115 mg.). There was thus obtained 3-acetoxymethyl-7-(imidazol-2-yl)aminoceph-3-em-1β-oxide-4-carboxylic acid trifluoroacetate, having the following n.m.r. spectrum in CD$_3$COOD: 2.0 (s, 3H); 3.44 (d, 1H); 3.97 (d, 1H); 4.65 (d, 1H); 4.95 (d, 1H); 5.23 (d, 1H); 5.8 (d, 1H); 6.87 (s, 2H).

EXAMPLE 2

To a solution of 3-chloro-7-(imidazol-2-yl)aminocephem-4-carboxylic acid trifluoroacetate as a mixture of delta-2 and delta-3 isomers (157 mg.) in acetic acid (4 ml.) cooled to 10° was dropwise aded peracetic acid (960 μl.) The temperature was allowed to rise to ambient temperature and the mixture was stirred for 2.5 hours. The suspension was filtered to obtain a white solid (27 mg.). The filtrate was evaporated in vacuo and the residue taken up in the minimum amount of a mixture of methanol and CH$_2$Cl$_2$. There was thus obtained a suspension which afforded a crystalline solid on filtration. The solids were combined to give 3-chloro-7-(imidazol-2-yl)aminoceph-3-em-4-carboxylic acid as a mixture of 1α and 1β oxides (61 mg.) containing 0.17 moles of trifluoroacetic acid and having the following n.m.r. spectrum in d$_6$ dimethyl sulphoxide+trifluoroacetic acid: 4.0 and 4.15 (s, 2H); 4.95 and 5.1 (d, 1H);5.7 and 5.8 (d, 1H); 7.05 (s, 2H).

The starting material may be obtained as follows:

To a solution of 2-fluoroimidazole hydrochloride (140 mg.) in methanol (0.4 ml.) was added a solution of diphenylmethyl 7-amino-3-chloroceph-3-em-4-carboxylate (400 mg.) in dimethylformamide (1 ml.) and the mixture was stirred at 70° for 4.5 hours. The solvent was evaporated in vacuo and the residue was purified by chromatography on silica gel at low temperature using CH$_2$Cl$_2$/methanol/acetic acid 100:6:4 v/v/v as eluant. There was thus obtained diphenylmethyl 3-chloro-7-(imidazol-2-yl)aminocephem-4-carboxylate hydrochloride as a 50:50 mixture of delta-2 and delta-3 isomers (260 mg.) having the following n.m.r. spectrum in CDCl$_3$+CD$_3$OD: 3.6–4.0 (m, 2H); 5.2–5.5 (m, 2H); 6.9 and 7.0 (s, 1H); 7.4 (s, 1H).

The above hydrochloride salt (242 mg.) was suspended in ethyl acetate and treated with aqueous sodium bicarbonate to liberature the free base. The organic layer was separated, dried and partially evaporated. A few drops of trifluoroacetic acid were then added, and the resulting mixture was evaporated to dryness. The residue was suspended in anisole (1 ml.) and trifluoroacetic acid (1 ml.) and the mixture stirred at ambient temperature for 0.5 hours. The solvent was evaporated and the residue was triturated with ether to give 3-chloro-7-(midazol-2-yl)aminocephem-4-carboxylic acid (126 mg.) as a mixture of delta-2 and delta-3 isomers, having the following n.m.r. spectrum in CDCl$_3$+CD$_3$OH: 3.4–3.6 (m); 4.85 (s); 5.1–5.6 (m, 2H); 6.35 (s); 6.8 (2s, 2H). This product contained a fraction of a mole of trifluoroacetic acid.

EXAMPLE 3

A solution of t-butyl 3-acetoxymethyl-7-(imidazol-2-yl)aminoceph-3-em-1α-oxide-4-carboxylate toluene-p-sulphonate (150 mg.) in trifluoroacetic acid (1.5 ml.) was stirred at ambient temperature for 40 minutes. The solvent was evaporated under reduced pressure and the residue precipitated from a solution in the minimum of acetone with CH$_2$Cl$_2$ to give 3-acetoxymethyl-4-(imidazol-2-yl)aminoceph-3-em-1α-oxide-4-carboxylic acid toluene-p-sulphonate as a beige powder (130 mg.) having the following n.m.r. in d$_6$ dimethyl sulphoxide+CD$_3$COOD: 2.05 (s, 3H); 2.28 (s, 3H); 3.75 (m, 2H); 4.65 (d, 1H); 5.05 (d, 1H); 5.05 (d, 1H); 5.7 (d, 1H); 7.08 (s, 2H); 7.3 (q, 4H).

The starting material may be prepared as follows:

To a solution of t-butyl 3-acetoxymethyl-7-ainoceph-3-em-1α-oxide-4-carboxylate (500 mg.) in chloroform/methanol (3:7 v/v; 2.5 ml.) was added 2-fluoroimidazol toluene-p-sulphonate (450 mg.) and the temperature of the mixture held at 65° for 6 hours. The solvent was evaporated under reduced pressure and the product purified by chromatography on silica (50 g.) at −10° using CH$_2$Cl$_2$/methanol/acetic acid 98.12:1.25:0.62 v/v/v as eluant. The purified product was precipitated from a solution in the minimum of CH$_2$Cl$_2$ with ether to give t-butyl 3-acetoxymethyl-7-(imidazol-2-yl)aminoceph-3-em-1α-oxide-4-carboxylate toluene-p-sulphonate (165 mg.) having the following n.m.r. in CDCl$_3$+CD$_3$COOD: 1.5 (s, 9H); 2.1 (s, 3H); 3.7 (m, 2H); 5 (m, t, 3H); 5.8 (m, 1H); 7.3 (s, 2H).

We claim:

1. A cephalosporin derivative of the formula I:

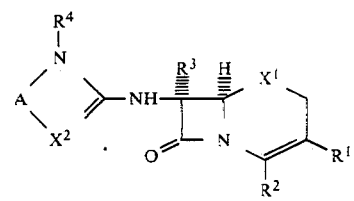

wherein $X^1$ is sulphinyl in which oxygen is in the β-configuration; $R^2$ is carboxy; $X^2$ is nitrogen; $R^3$ is hydrogen; A is of the formula II:

in which $R^6$ and $R^7$ are hydrogen; $R^4$ is hydrogen; and $R^1$ is hydrogen, chlorine, methyl, acetoxymethyl, 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-isopropyl-1H-tetrazol-5-ylthiomethyl, 1-(2,2,2-trifluoro)ethyl-1H-tetrazol-5-ylthiomethyl, 1-phenyl-1H-tetrazol-5-ylthiomethyl, 1-(2-methylthio)ethyl-1H-tetrazol-5-ylthiomethyl, 1,3,4-thiadiazol-2-ylthiomethyl, 5-methyl-1,3,4-thiadiazol-2-ylthiomethyl, 1,2,3-thiadiazol-5-ylthiomethyl, 1H-1,2,3,-triazol-4-ylthiomethyl, 5-trifluoromethyl-1H-1,2,4-triazol-3-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-carboxymethyl-7-hydroxypyrrolo[1,2-b]pyridazin-2-yl)thiomethyl, methoxymethyl, hydroxymethyl, azidomethyl, aminomethyl, benzoyloxymethyl, acetylaminomethyl, carbamoyloxymethyl, 2-methylthio-1,3,4-thiadiazol-5-ylthiomethyl, 2-mercapto-1,3,4-thiadiazol-5-ylthiomethyl, 2-acetylamino-1,3,4-thiadiazol-5-ylthiomethyl, 5-methyl-1,2,4-thiadiazol-2-ylthiomethyl, 2-sulphomethyl-1,2,4-oxadiazol-5-ylthiomethyl, 4-methyl-5-(3-carboxypropyl)thiazol-2-ylthiomethyl, 2H-2-methyl-1,2,3-triazol-4-ylthiomethyl, 1H-1,2,4-triazol-2-ylthiomethyl, 4,5-dihydro-6-hydroxy-4-methyl-5-oxo-1,2,4-triazin-3-ylthiomethyl, 2,5-dihydro-6-hydroxy-2-methyl-5-oxo-1,2,4-triazin-3-ylthiomethyl, 1-oxidopyrid-2-ylthiomethyl, imidazo[4,5-b]pyrid-2-ylthiomethyl or imidazo[4,5-b]-pyrimidin-2-ylthiomethyl, or the pharmaceutically-acceptable acid- or base- addition salts thereof.

2. A cephalosporin derivative of the formula I given in claim 1 in which $R^1$ is 1H-1,2,3-triazol-4-ylthiomethyl, methyl or acetoxymethyl.

3. The compound 3-acetoxymethyl-7-(imidazol-2-yl)aminoceph-3-em-1α-oxide-4-carboxylic acid, and the pharmaceutically acceptable acid-addition salts and base-addition salts thereof.

4. A pharmaceutical composition which comprises an antibacterially-effective amount of a cephalosporin derivative as claimed in claim 1 in association with a pharmaceutically-acceptable diluent or carrier.

5. A method of treating a bacterial infection in a warm-blooded animal which comprises administering to the animal a therapeutically effective amount of the compound of claim 1.

* * * * *